United States Patent [19]
Wasylyk et al.

[11] Patent Number: 6,028,245
[45] Date of Patent: Feb. 22, 2000

[54] TRANSGENIC ANIMALS OVEREXPRESSING MDM2

[75] Inventors: Bohdan Wasylyk, Illkirsch; Bruno Tocqué, Courbevoie; Moussa Alkhalaf, Renne, all of France

[73] Assignees: Rhone-Poulenc Rorer SA, Antony Cedex; Institut National de la Sante et de la Recherche Medicale, Paris, both of France

[21] Appl. No.: 09/104,497

[22] Filed: Jun. 25, 1998

Related U.S. Application Data

[60] Provisional application No. 60/051,739, Jul. 3, 1997.

[51] Int. Cl.[7] .................................................. C12N 15/00
[52] U.S. Cl. ................................... 800/18; 800/3; 800/8; 800/9; 800/13; 800/14; 435/440; 435/455
[58] Field of Search ................................ 800/3, 8, 9, 13, 800/14, 18

[56] References Cited

PUBLICATIONS

Fakharzadeh et al., Tumorigenic potential associated with enhanced expression of a gene that is amplified in a mouse tumor cell line, The EMBO Journal 10(6), 1565–1569 (1991).
Bank et al., Enhanced binding of a 95 kDa protein to p53 cells undergoing p54–mediated growth arrest, The EMBO Journal 11(6), 2115–2121 (1992).
Dubs–Poterszman et al., MDM2 transformation in the absence of p53 and abrogation of the p107 G1 cell–cycle arrest, Oncogene 11, 2445–2449 (1995).
Momand et al., The mdm–2 Oncogene Product Forms a Complex with the p53 Protein and Inhibits p53–Mediated Transactivation, Cell 69, 1237–1245 (1992).
Sigalas et al., Alternatively spliced mdm2 transcripts with loss of p53 binding domain sequences: Transforming ability and frequent detection in human cancer, Nature Medicine, 2(8), 912–917 (1996).
Jones et al., Rescue of embryonic lethality in Mdm2–deficient mice by absence of p53, Nature 378, 206–208 (1995).
Montes de Oca Luna et al., Rescue of early embryonic lethality in mdm2–deficient mice by deletion of p53, Nature 378, 203–206 (1995).
Oliner et al., Amplification of a gene encoding a p53–associated protein in human sarcomas, Nature 358, 80–83 (1992).
Oliner et al. Oncoprotein MDM2 conceals the activation domain of tumor suppressor p53, Nature 362, 857–860 (1993).
Fiddler et al., Amplification of MDM2 Inhibits MyoD–Mediated Myogenesis, Molecular & Cellular Biology 16(9), 5048–5057 (1996).
Finlay, The mdm–2 Oncogene Can Overcome Wild–Type p53 and mdm2 Proteins, Molecular & Cellular Biology, 13(1), 301–306 (1993).

Haines et al., Physical & Functional Interaction between Wild–Type p53 and mdm2 Proteins, Molecular & Cellular Biology 14(2), 1171–1178 (1994).
Chen et al., mdm–2 Inhibits the G1 Arrest and Apoptosis Functions of the p53 Tumor Suppressor Protein, Molecular & Cellular Biology 16(5), 2445–2452 (1996).
Chen et al., Mapping of the p53 and mdm–2 Interaction Domains, Molecular & Cellular Biology 13(7), 4107–4114 (1993).
Haupt et al., Cell type–spcific inhibition of p53–mediated apoptosis by mdm2, The EMBO Journal 15(7), 1596–1606 (1996).
Leach et al. p53 Mutation and MDM2 Amplification in Human Soft Tissue Sarcomas, Cancer Research 53, 2231–2234 (1993).
Cordon–Cardo et al., Molecular Abnormalities of mdm2 and p53 Genes in Adult Soft Tissue Sarcomas, Cancer Research 54, 794–799 (1994).
Wu et al., The p53–mdm–2 autoregulatory feedback loop, Genes & Development 7, 1126–1132 (1993).
Cahilly–Snyder et al., Molecular Analysis and Chromosomal Mapping of Amplified Genes Isolated from a Transformed Mouse 3T3 Cell Line, Somatic Cell & Molecular Genetics 13(3) 235–244 (1987).
Epstein, The genetics of human skin diseases, Current Opinion in Genetics & Development 6, 295–300 (1996).
Williams, Ichthyosis: Mechanisms of Disease, Pediatric Dermatology 999(4), 365–368 (1992).
Wall, RJ Transgenic Livestock: Progress and prospects for the future. Theriogenology 45: 57–68, 1996.
Mullins et al. Fulminant hyoertension in transgenic rats harboring the mouse Ren–2 gene. Nature 344: 541–544, Apr. 1990.
Hammer et al. Spontaneous inflammatory disease in transgenic rats expressing HLA–B27 and human b2m: An animal model of HLA–B27–associated disorders. Cell 63: 1099–1112, Nov. 1990.
Mullins et al. Expression of the DBA/2J ren–2 gene in the adrenal gland of transgenic mice. EMBO J. 8: 4065–4072, 1989.
Taurog et al. HLA–B27 in inbred and non–inbred transgenic mice. J. Immunol. 141: 4020–4023, Dec. 1988.
Lundgren et al. Targeted expression of MDM2 uncouples S phase from mitosis and inhibits mammary gland development independent of p53. Genes and Devlopment 11(6): 714–725, Mar. 1997.

*Primary Examiner*—Bruce R. Campell
*Assistant Examiner*—Anne-Marie Baker

[57] ABSTRACT

The present invention relates to transgenic, non-human animals overexpressing a MDM2 gene. These animals model MDM2 over-expression associated with human tumors, display a major phenotype characterized by the severe skin disorder ichthyosis, and are useful for identifying compounds for the treatment of human disease. Therefore, the invention also relates to methods of using the animals for identifying compounds effective for the treatment of diseases of the skin and respiratory tract, and to the compounds themselves.

8 Claims, 8 Drawing Sheets

FIG. 6A
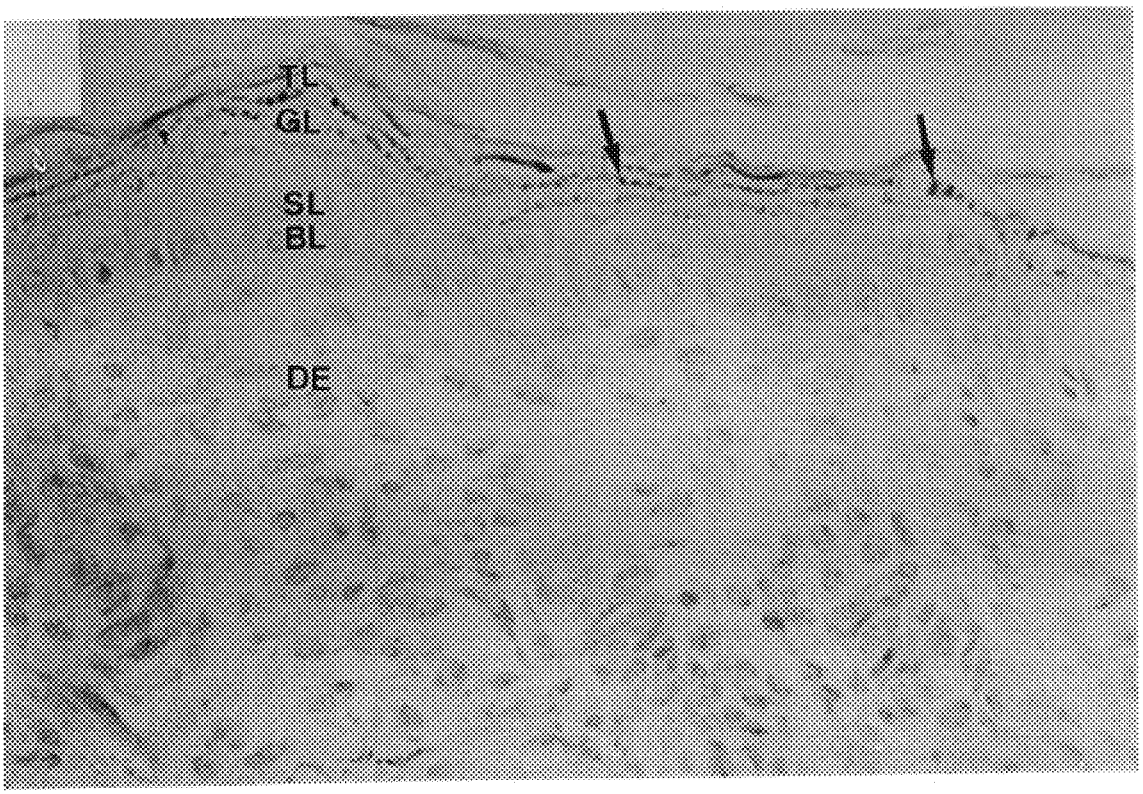
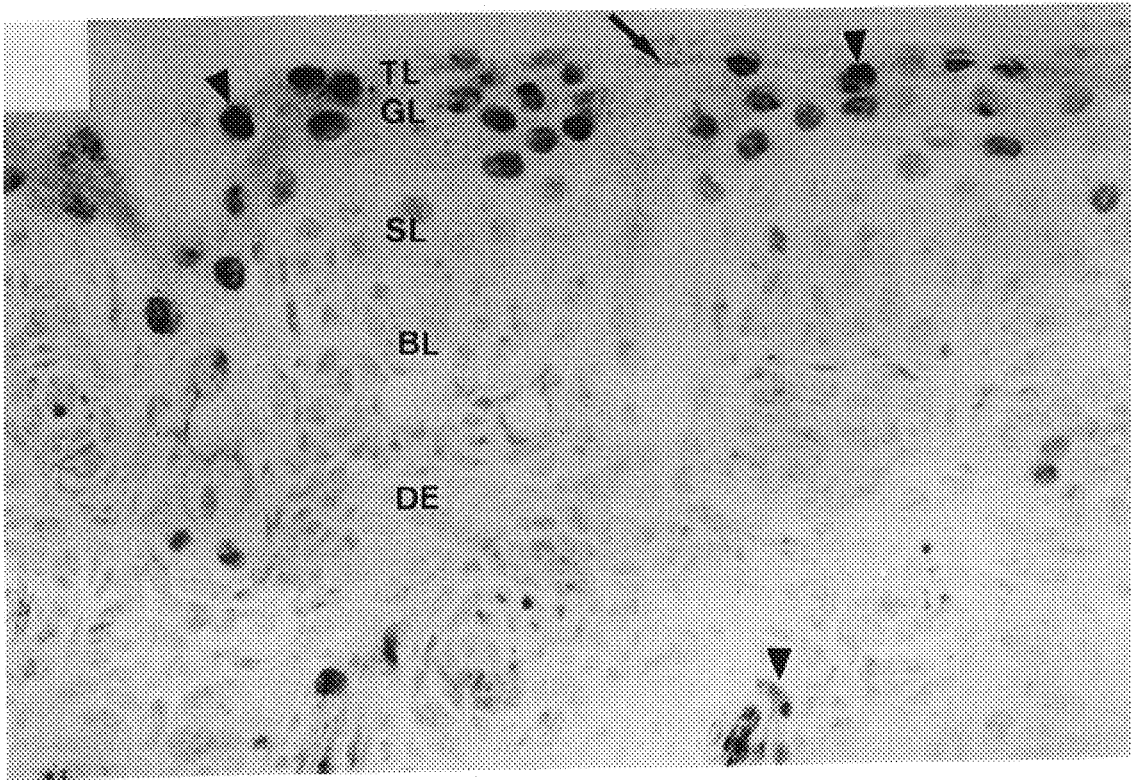
FIG. 6B

| FIG. 8A | FIG. 8B | FIG. 8C | FIG. 8D |
|---|---|---|---|
|  | 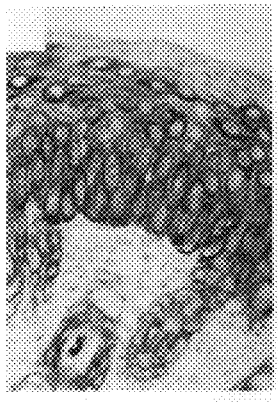 | 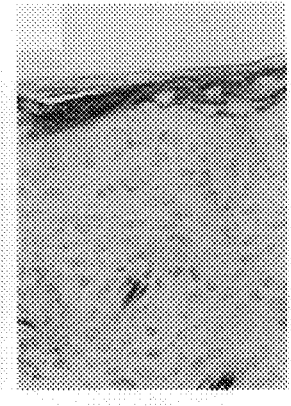 | 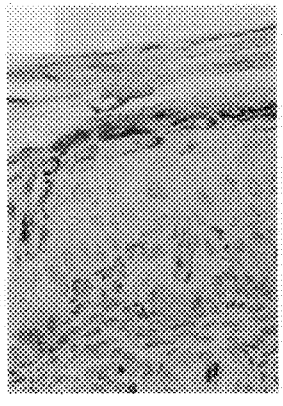 |
|  | 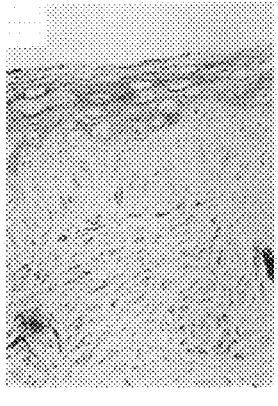 |  | 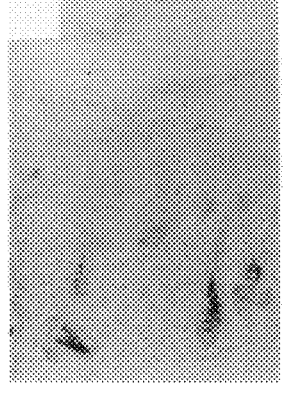 |
| FIG. 8E | FIG. 8F | FIG. 8G | FIG. 8H | ns
TRANSGENIC ANIMALS OVEREXPRESSING MDM2

This application claims the benefit of U.S Provisional Application No. 60/051,739 filed Jul. 3, 1997.

FIELD OF THE INVENTION

The present invention relates to models of human disseases, to methods of using these models for identifying compounds effective for the treatment of these diseases, and to the compounds themselves. In particular, the invention relates to transgenic animals overexpressing a MDM2 gene. These animals model MDM2 over-expression associated with human tumors, display a major phenotype characterized by a severe skin disorder, and are useful for identifying compounds for the treatment of human disease.

BACKGROUND OF THE INVENTION

Ichthyosis

There are several known genetic diseases of the skin. For example, defects in the gene encoding steroid sulphatase are associated with X-linked ichthyosis, defects in K1 and K10 keratin genes are linked to epidermolytic hyperkeratosis and defects in the gene encoding transglutaminase I are associated with lamellar ichthyosis (Epstein, 1996; Williams, 1992). Ichthyosis vulgaris, on the other hand, has no known molecular defect.

Ichthyosis vulgaris is an autosomal dominant genetic and acquired skin disorder affecting about 1/300 individuals. Characteristics of ichthyosis vulgaris include a scaly "fish-skin" appearance with abnormal desquamation, epidermal hyperproliferation, lack of production of keratohyalin granules, and hyperkeratosis, exemplified by the cornified layer containing an excess of incompletely differentiated corneocytes and a defective barrier function. There is currently a need in the industry for models of ichthyosis vulgaris, including animal models, to enable screening and identification of compounds for the treatment of this disease.

MDM2

The MDM2 (murine double minute 2) gene was originally discovered as an oncogene that is amplified in the spontaneously transformed BALB/c 3T3DM cell line (Cahilly-Snyder et al., 1987; Fakharzadeh et al., 1991). MDM2 over-expression was subsequently implicated in the pathogenesis of human neoplasia via inhibition of the p53 tumor-suppressor protein (Chen et al, 1996; Cordon-cardo et al., 1993; Finlay, 1993; Haines at al., 1994; Haupt et al., 1996; Leach et al;, 1993, Momand et al, 1992; Oliner et al. 1992; Oliner et al., 1993; Wu et al., 1993). Specifically, the MDM2 gene was found to encode a 90 kD protein capable of forming a complex with p53, inhibiting the tumor suppressor protein's ability to activate transcription and induce apoptosis (Barak et al., 1992; Chen et al., 1993; Finlay, 1993; Haines et al., 1994; Haupt et al., 1996; Momand et al, 1992; Oliner et al., 1993; Wu et al., 1993).

The human MDM2 gene (hMDM2) has been found to be amplified or overexpressed in a significant number of human tumors containing wild type p53 (Oliner et al. 1992; Cordon-cardo et al., 1993; Leach et al, 1993). Negative regulation of p53 by MDM2 has been shown to be essential during mouse development since MDM2 null mice exibit embryonic lethality shortly after implantation but MDM2/p53 double knock out mice are viable (Montes de Luca et al., 1995; Jones et al., 1995). However, there are several indications that inhibition of p53 activity is not the only function of MDM2. In particular, MDM2 can transform cells in the absence of p53 (DubsPottersman et al, 1995). Sigalas et al. (1996) showed that alternatively spliced forms of MDM2 that lack p53 binding domain are able to transform NIH3T3 cells and are found more frequently in poorly differentiated tumors. MDM2 inhibits MyoD function, resulting in a dominant non-differentiating phenotype in muscle (Fiddler et al., 1996).

MDM2 is expressed in skin and appears to be particularly important in skin function. MDM2 is also expressed in respiratory epithelium during mouse development, suggesting that it may have an important role in other epithelia. Preliminary evidence indicates that MDM2 is predominantly expressed in the basal layer, where the amounts decrease upon differentiation. This suggests that MDM2 is involved in cell division in the basal layer, and that the hyperproliferative defect of ichthyosis is treatable by decreasing MDM2 levels. There are, however, no current models for studying ichthyosis, or for screening potential therapeutic compounds for this disease. The present invention overcomes these problems.

SUMMARY OF THE INVENTION

The present invention provides model systems for studying diseases including icthyosis, and for screening compounds useful for the treatment of these diseases.

Therefore, a first aspect of the invention provides a transgenic non-human animal comprising a MDM2 gene or variant thereof, and capable of overexpressing said gene.

Another aspect provides a transgenic non-human animal comprising a human MDM2 gene or variant thereof, and capable of overexpressing said gene.

In a preferred embodiment of the invention, the MDM2 gene is operably linked to a strong promoter, such as a HCMV promoter. Transgenic animals comprising such a construct provide a model of ichthyosis. The animal is preferably a rodent, such as a mouse.

In further embodiments of the invention the MDM2 gene is operably linked to a tissue specific promoter in order to localise MDM2 over-expression to particular skin cells, which may be located within a particular layer of the skin. Preferred tissue specific promoters include the keratin 5 (K5) and keratin 14 (K14) promoters for the basal layer of skin; keratin 1 (K1) and keratin 10 (K10) promoters for the suprabasal layer of skin; loricrin, involucrin and transglutaminase I promoters for the granular layer of skin; cornifin β promoter for squamous epithelia, and mCC10 and elastin promoters for the respiratory epithelium.

Another aspect of the invention provides a transgenic non-human animal comprising a MDM2 gene or variant thereof, and capable of overexpressing said gene, wherein said gene is operably linked to a sequence encoding a mutated ligand binding domain from a glutacorticoid or oestrogen receptor fused to said MDM2. In this embodiment expression of said gene is regulated by glucocorticoids or tamoxifen.

Still another aspect of the invention provides methods of determining the ability of a compound to modulate MDM2 function in a cell. Preferred methods comprise administering a compound to a transgenic non-human animal comprising a MDM2 gene and comparing MDM2 function to that in control animals.

In still another aspect, the invention provides methods for identifying a compound effective for the treatment of diseases of the skin or respiratory tract comprising administering a compound to a transgenic non-human animal comprising a MDM2 gene and capable of overexpressing said gene. Preferred diseases include skin disorders such as ichthyosis, psoriasis and eczema. Additional disorders associated with MDM2 over-expression include tumors, asthma, and allergic rhynitis.

In still another aspect the invention provides a method for modulating MDM2 function in a cell by administering to the cell a compound capable of modulating MDM2 levels and/or biological activity within the cell. In a preferred aspect of the invention the cells are cells of a patient suffering from a disease of the skin or respiratory tract, and the method comprises administering to the cells of a patient a compound capable of modulating MDM2 function. Such diseases include ichthyosis, psoriasis, tumors, asthma, eczema, and allergic rhynitis.

A) Schematic drawing showing structure of the HCMV/MDM2 hybrid transcription unit. Oligonucleotides NX30 and SC205 to SC209 were used for screening transgenic founders and for the reverse transcriptase PCR analysis.

B) Six transgenic lines were generated. Transgene expression in skin was moderate in lines HCMV5, 19 and 20. Lines HCMV21, 25 and HCMV25/p53−/− background show higher level of expression. A line designated HCMV21/p53−/− shares a very similar phenotype to line HCMV21 (data not shown).

FIGS. 2(A to D): Gross phenotype exhibited by HCMV/MDM2 transgenic mice.

A and C: Wild Type mice at 4 days age. Ventral and dorsal views respectively.

B and D: Typical appearance of severely phenotypic MDM2 transgenic mice characterised by the scaly "fish skin" aspect and desquamations.

Figure 3A:
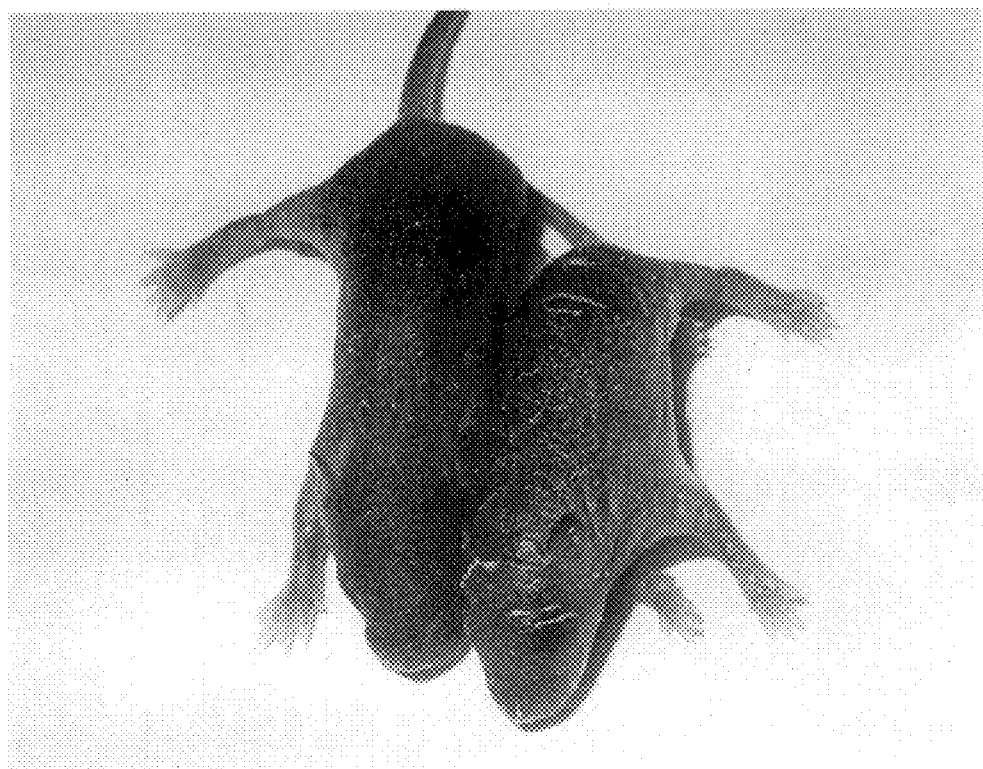
Figure 3B:
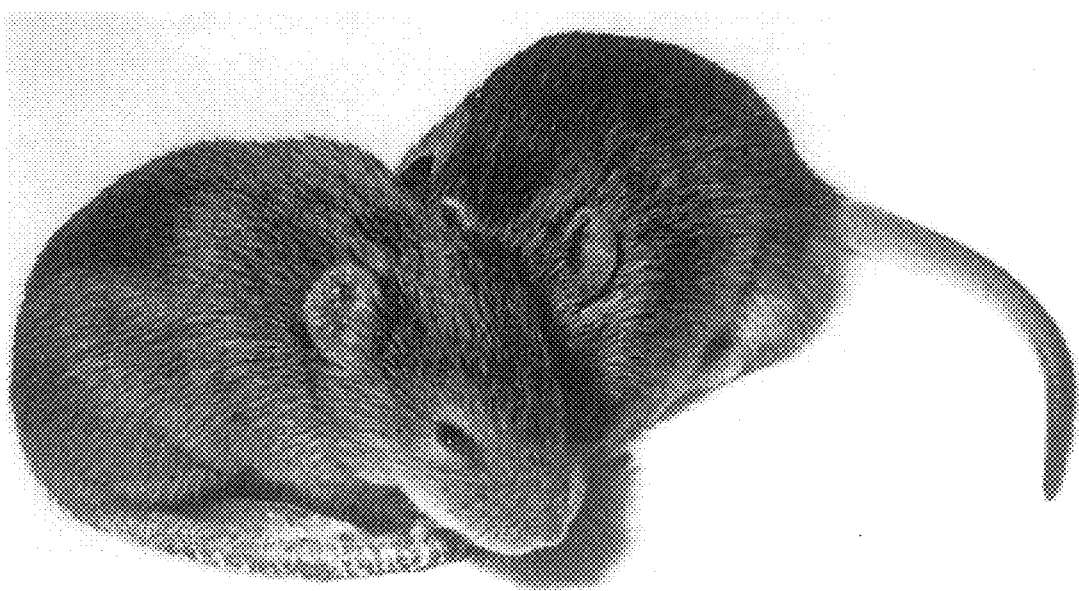
Figure 4A:
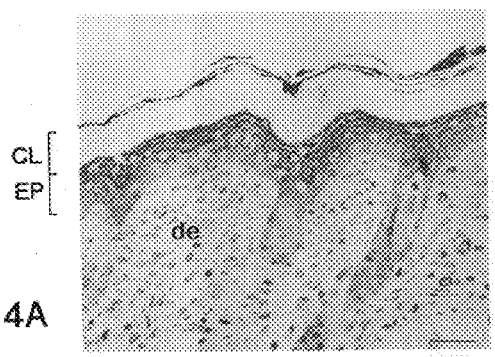
Figure 4B:
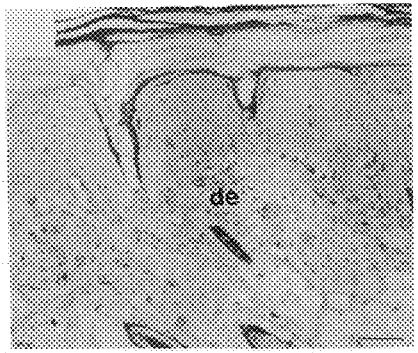
Figure 4C:
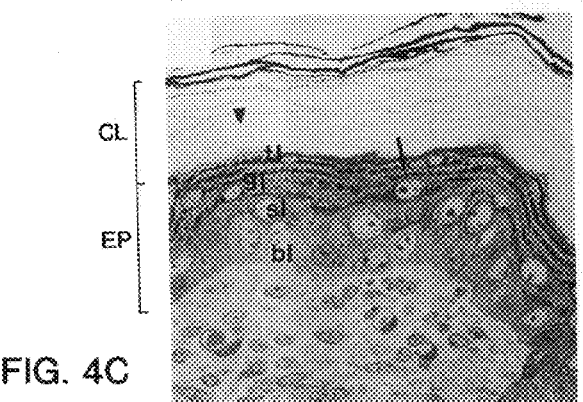
Figure 4D:
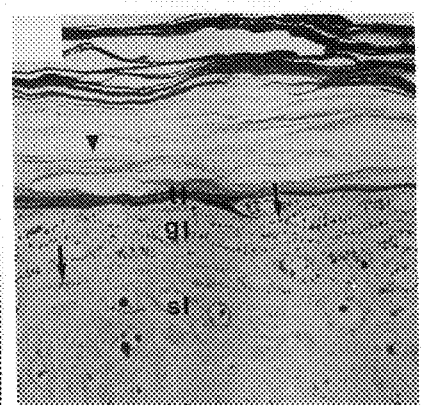
Figure 5A:
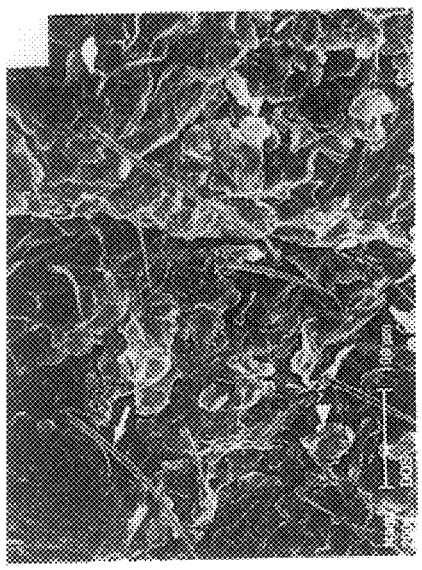
Figure 5B:
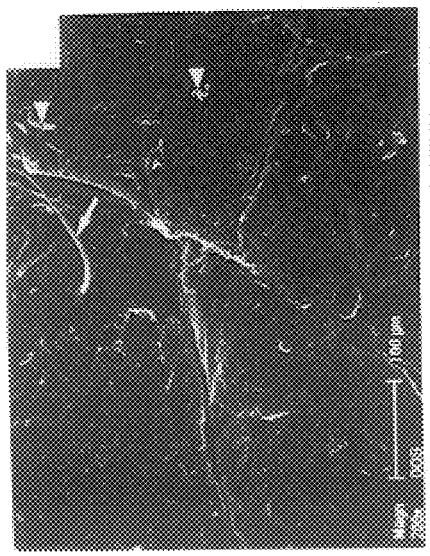
Figure 5C:
Figure 5D:
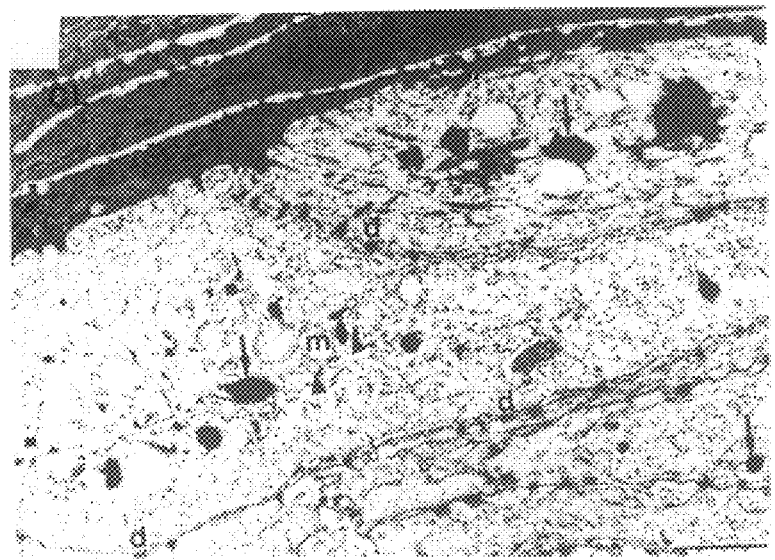

FIGS. 3(A and B): Gross appearance of HCMV25/MDM2 transgenic on p53−/− background.

A) Gross phenotype of HCMV/MDM2 transgenic mouse on p53−/− background (Right) as compared to non MDM2 transgenic p53−/− littermate mouse (Left) at 4 days old.

B) Same as in A, but at 2 weeks old. Note that tail and ear of the transgenic mouse still show the skin abnormality phenotype (left). On the right is the wild type littermate.

FIGS. 4(A to D): Histopathology of transgenic epidermis.

A) p53+/+ wt control

B) HCMV25/p53+/+

C) p53−/− wt control

D) HCMV25/p53−/−

Note that the epidermis (EP) and the granular layer (gl) are thicker than in controls. The keratohyalin granules (arrows) are smaller and reduced in density. The cornified layer (CL) contains more cellular material when compared to controls.

FIGS. 5(A to D): Electron Microscopy analysis of HCMV/MDM2 transgenic mice.

A–B: Scanning Electron Microscopy analysis of the epidermal surface. Note that in transgenic mice (B) the stratum corneum layer is not present, resulting in the direct exposure of the granular layer to the outside enviroment. Note that there is less hair (arrows). The control epidermal surface is protected by the cornified layer (see arrowheads) (A).

C–D. Transmission Electron Microscopy of the granular layer. C) Ultrastructural appearance of normal epidermal granular layer showing the keratohyalin granules. P-F granules (arrows), L-granules (arrowheads) D) Transgenic epidermal granular cells showing a reduced number of L and P-F granules. Note that the size of P-F granules is reduced in transgenic cells. mitochondria (m), desmosome(d), Cornified layer (CL)

FIGS. 6(A and B): The localization of MDM2 transgene expression.

A) Control mice with no obvious positive nuclei after immunolabeling with MDM2 antibody (PAB 365). Note the presence of keratohyalin granules (arrows). Transition Layer (TL), Granular Layer (GL), Spinous Layer (SL), Basal Layer (BL), dermis (DE).

B) transgenic skin showing high levels of MDM2 in the granular layer, the strongest level of expression is localized in the outermost granular cells (arrowheads).

FIGS. 7(A to F): BrdU incorporation and induction of apoptosis by MDM2 in transgenic mice skin.

A) BrdU incorporation in wild type mouse skin. Few nuclei are labeled in the basal layer (bl) (arrows).

B) Transgenic epidermis with many cells showing BrdU incorporation in the basal layer (bl). No positive cells were found in the other cell layers of the epidermis. Dermis (de).

C and E) Skin section from 5 day old wild type mice (p53+/+) and from p53−/− mice (E) with no obvious cells in apoptosis. tl (transtion layer), ep (epidermis) and de (dermis).

D and F) Transgenic skin from p53+/+ mice (D) or p53−/− mice (F). Note the presence of typical round cells with labeled nuclei in the transition layer. In this layer the dying cells show a fragmented nuclei (arrows).

FIGS. 8(A–F): Altered expression of Cytokeratin 14, Filaggrin, Involucrin and Loricrin in MDM2 transgenic mice.

A–B: Immunostaining with an anti-K14 antibody. (A) shows a control section with a region of limited K14 staining in the basal layer.(B) shows more extended K14 staining throughout the whole epidermis.

C–D: Immunostaining with an anti-filaggrin antibody. (C) shows a control skin. Note the low level of staining in the granular layer of transgenic mouse skin (D).

E–F: immunostaining with an anti-involucrin antibody. The control (E) shows a dense staining in the granular layer. Less dense and more diffused staining were observed in transgenic mouse skin (F).

DETAILED DESCRIPTION OF THE INVENTION

Definitions

The following defined terms are used throughout the present specification, and should be helpful in understanding the scope and practice of the present invention.

A "polypeptide" is a polymeric compound comprised of covalently linked amino acid residues. Amino acids have the following general structure:

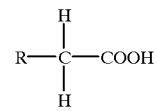

Amino acids are classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

A "protein" is a polypeptide which plays a structural or functional role in a living cell.

The polypeptides and proteins of the invention may be glycosylated or unglycosylated.

A "variant" of a polypeptide or protein is any analogue, fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification. Variants also include a related protein having substantially the same biological activity, but obtained from a different species.

The skilled artisan can produce variants having single or multiple amino acid substitutions, deletions, additions, or replacements. These variants may include, inter alia: (a) variants in which one or more amino acid residues are substituted with conservative or non-conservative amino acids, (b) variants in which one or more amino acids are added to the polypeptide or protein, (c) variants in which one or more of the amino acids includes a substituent group, and (d) variants in which the polypeptide or protein is fused with another polypeptide such as serum albumin. The techniques for obtaining these variants, including genetic (suppressions, deletions, mutations, etc.), chemical, and enzymatic techniques, are known to persons having ordinary skill in the art.

If such allelic variations, analogues, fragments, derivatives, mutants, and modifications, including alternative mRNA splicing forms and alternative post-translational modification forms result in derivatives of the polypeptide which retain any of the biological properties of the polypeptide, they are intended to be included within the scope of this invention.

A "nucleic acid" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes cDNA, genomic DNA, synthetic DNA, and semi-synthetic DNA. The sequence of nucleotides that encodes a protein is called the sense sequence.

A "MDM2 gene" is any gene which encodes a MDM2 protein. Preferred MDM2 genes encode murine or human MDM2.

"Regulatory region" means a nucleic acid sequence which regulates the expression of a second nucleic acid sequence. A regulatory region may include sequences which are naturally responsible for expressing a particular nucleic acid (a homologous region) or may include sequences of a different origin (responsible for expressing different proteins or even synthetic proteins). In particular, the sequences can be sequences of eukaryotic or viral genes or derived sequences which stimulate or repress transcription of a gene in a specific or non-specific manner and in an inducible or non-inducible manner. Regulatory regions include origins of replication, RNA splice sites, enhancers, transcriptional termination sequences, signal sequences which direct the polypeptide into the secretory pathways of the target cell, and promoters.

A regulatory region from a "heterologous source" is a regulatory region which is not naturally associated with the expressed nucleic acid. Included among the heterologous regulatory regions are regulatory regions from a different species, regulatory regions from a different gene, hybrid regulatory sequences, and regulatory sequences which do not occur in nature, but which are designed by one having ordinary skill in the art.

A "vector" is any means for the transfer of a nucleic acid into a host cell. The term "vector" includes both viral and nonviral means for introducing the nucleic acid into a cell in vitro, ex vivo or in vivo. Non-viral vectors include plasmids, liposomes, electrically charged lipids (cytofectins), DNA-protein complexes, and biopolymers. Viral vectors include retrovirus, adeno-associated virus, pox, baculovirus, vaccinia, herpes simplex, Epstein-Barr and adenovirus vectors. In addition to a nucleic acid according to the invention, a vector may also contain one or more regulatory regions, and/or selectable markers useful in selecting, measuring, and monitoring nucleic acid transfer results (transfer to which tissues, duration of expression, etc.).

Transgenic Animals

The term "animal" is used herein to include all vertebrate animals, except humans. It also includes an individual animal in all stages of development, including embryonic and fetal stages. A "transgenic animal" is an animal containing one or more cells bearing genetic information received, directly or indirectly, by deliberate genetic manipulation at a subcellular level, such as by microinjection or infection with recombinant virus. This introduced DNA molecule may be integrated within a chromosome, or it may be extra-chromosomally replicating DNA. The term "germ cell-line transgenic animal" refers to a transgenic animal in which the genetic information was introduced into a germ line cell, thereby conferring the ability to transfer the information to offspring. If such offspring in fact possess some or all of that information, then they, too, are transgenic animals.

The information may be foreign to the species of animal to which the recipient belongs, foreign only to the particular individual recipient, or genetic information already possessed by the recipient. In the last case, the introduced gene may be differently expressed compared to the native endogenous gene.

The genes may be obtained by isolating them from genomic sources, by preparation of cDNAs from isolated RNA templates, by directed synthesis, or by some combination thereof.

To be expressed, a gene should be operably linked to a regulatory region. Regulatory regions, such as promoters, may be used to increase, decrease, regulate or designate to certain tissues or to certain stages of development the expression of a gene. The promoter need not be a naturally occurring promoter. The "transgenic non-human animals" of the invention are produced by introducing "transgenes" into the germline of the non-human animal. The methods enabling the introduction of DNA into cells are generally available and well-known in the art. Different methods of introducing transgenes could be used. Generally, the zygote is the best target for microinjection. In the mouse, the male pronucleus reaches the size of approximately 20 $\mu$m in diameter, which allows reproducible injection of 1–2 pL of DNA solution. The use of zygotes as a target for gene transfer has a major advantage. In most cases, the injected DNA will be incorporated into the host gene before the first cleavage (Brinster, et al., 1985). Consequently, nearly all cells of the transgenic non-human animal will carry the incorporated transgene. Generally, this will also result in the efficient transmission of the transgene to offspring of the founder since 50% of the germ cells will harbor the transgene. Microinjection of zygotes is a preferred method for incorporating transgenes in practicing the invention.

Retroviral infection can also be used to introduce a transgene into a non-human animal. The developing non-human embryo can be cultured in vitro to the blastocyst stage. During this time, blastomeres may be targets for retroviral infection (Jaenich, R. 1976). Efficient infection of the blastomeres is obtained by enzymatic treatment to remove the zona pellucida (Hogan et al., 1986). The viral vector system used to introduce the transgene is typically a replication-defective retrovirus carrying the transgene (Jahner et al., 1985; Van der Putten et al., 1985). Transfection is easily and efficiently obtained by culturing the blastomeres on a monolayer of virus-producing cells (Van der Putten, supra; Stewart et al., 1987). Alternatively, infection can be performed at a later stage. Virus or virus-producing cells can be injected into the blastocoele (Jahner et al., 1982). Most of the founder animals will be mosaic for the transgene since incorporation occurs only in a subset of the cells which formed the transgenic non-human animal. Furthermore, the founder animal may contain retroviral insertions of the transgene at a variety of positions in the genome; these generally segregate in the offspring. In addition, it is also possible to introduce transgenes into the germ line, albeit with low efficiency, by intrauterine retroviral infection of the midgestation embryo (Jahner et al., (1982) supra).

A third type of target cell for transgene introduction is the embryonal stem cell (ES). ES cells are obtained from pre-implantation embryos cultured in vitro (Evans, M. J., et al., 1981; Bradley, A., et al. 1984; Gossler, et al., 1986; and Robertson, et al., 1986). Transgenes can be efficiently introduced into ES cells by DNA transfection or by retrovirus-mediated transduction. The resulting transformed ES cells can thereafter be combined with blastocysts from a non-human animal. The ES cells colonize the embryo and contribute to the germ line of the resulting chimeric animal (For review see Jaenisch, R., 1988).

The methods for evaluating the presence of the introduced DNA as well as its expression are readily available and well-known in the art. Such methods include, but are not limited to DNA (Southern) hybridization to detect the exogenous DNA, polymerase chain reaction (PCR), polyacrylamide gel electrophoresis (PAGE) and Western blots to detect DNA, RNA and protein. The methods include immunological and histochemical techniques to detect expression of a MDM2 gene.

As used herein, a "transgene" is a DNA sequence introduced into the germline of a non-human animal by way of human intervention such as by way of the Examples described below.

Nucleic Acids

The present invention relates to the discovery that animals model overexpressing a MDM2 gene display a major phenotype characterized by a severe skin disorder, and that MDM2 over-expression inhibits skin-cell differentiation and potently induces apoptosis.

Transgenic animals according to the invention comprise a nucleic acid sequence comprising a gene encoding MDM2 or variant thereof, and are capable of overexpressing the gene. The nucleic acid may be of natural or artificial origin. It may be genomic DNA (gDNA), complementary DNA (cDNA), hybrid sequences or synthetic or semisynthetic sequences. It may be of human, animal, plant, bacterial or viral origin and the like. It may be obtained by any technique known to persons skilled in the art, and especially by screening libraries, by chemical synthesis, or alternatively by mixed methods including chemical or enzymatic modification of sequences obtained by screening libraries. It is preferably cDNA or gDNA. The complete DNA and amino acid sequences for murine and human MDM2 are disclosed in Fakharzadeh et al. (1991) and Oliner et al. (1992), respectively, the entire contents of which are incorporated herein by reference.

Regulatory Regions

Generally, the gene encoding MDM2 or variant thereof is linked to one or more regulatory regions. Selection of the appropriate regulatory region or regions is a routine matter, within the level of ordinary skill in the art.

The regulatory regions may comprise a promoter region for functional transcription, as well as a region situated in 3' of the gene of interest, and which specifies a signal for termination of transcription and a polyadenylation site. All these elements constitute an expression cassette.

Promoters that may be used in the present invention include both constitutive promoters and regulated (inducible) promoters. The promoter may be naturally responsible for the expression of the nucleic acid. It may also be from a heterologous source. In particular, it may be promoter sequences of eukaryotic or viral genes. For example, it may be promoter sequences derived from the genome of the cell which it is desired to infect. Likewise, it may be promoter sequences derived from the genome of a virus, including the adenovirus used. In this regard, there may be mentioned, for example, the promoters of the ElA, MLP, HCMV and RSV genes and the like. In addition, the promoter may be modified by addition of activating or regulatory sequences or sequences allowing a tissue-specific or predominant expression.

Preferred tissue specific promoters include the keratin 5 (K5) (Missero et al., 1993) and keratin 14 (K14) (Wang et al., 1997) promoters for the basal layer of skin; keratin 1 (K1) (Johnson et al., 1985) and keratin 10 (K10) (Feng et al., 1997) promoters for the suprabasal layer of skin; loricrin (Yoneda et al., 1993), involucrin (Carroll et al., 1997; Carroll et al., 1995) and transglutaminase I (Lee et al., 1996) promoters for the granular layer of skin; cornifin β promoter (Austin et al., 1996) for squamous epithelia, and mCC10 (Ray et al., 1996) and elastin (Hsu-Wong et al., 1994) promoters for the respiratory epithelium.

Tissue specific promoters provide the means for modelling a variety of skin diseases. The molecular basis of some skin diseases, such as keratodermas, is known to be due to mutations in keratin genes or to genes involved in epidermal growth and differentiation. For example, keratins 5 and 14 are expressed in the basal keratinocytes and mutations in either of these genes cause the blistering disorder epidermolysis bullosa simplex. Mutations affecting the gene encoding suprabasal keratins 1 and 10 underlie the clinical phenotype of epidermolytic hyperkeratosis. A novel mutation in the loricrin gene was recently described in Vohwinkel syndrome (Nat. Genet. 13:70–77, 1996). Over-expression of a MDM2 gene specifically in restricted skin areas such as the basal layer (using CK 5 and CK 14 promoters), suprabasal layer (using CK 1 and CK 10 promoters) and in the cornified layer (using loricrin promoter) will produce disorders corresponding to those generated by keratin gene mutations. Similarly, prolonged MDM2 expression in the basal layer will generate basal cell carcinoma.

Alternatively, the MDM2 gene or variant thereof may be operably linked to a sequence encoding a mutated ligand binding domain from a glutacorticoid or oestrogen receptor fused to said MDM2. In this case, expression of the gene is regulated by glucocorticoids or tamoxifen.

When the nucleic acid does not contain promoter sequences, one may be inserted.

Additional promoters useful for practice of this invention are the ubiquitous promoters HPRT (Rincon-Limas et al., 1994), vimentin (Vicart et al., 1994), actin (Bronson et al., 1996), and tubulin (Gloster et al., 1994); the intermediate filament promoters desmin (Lee et al., 1995), neurofilaments, keratin, and GFAP (Galou et al., 1994); the therapeutic gene promoters MDR (Yang et al., 1996), CFTR (Matthews et al., 1996), and factor VIII (McGlynn et al., 1996); promoters which are preferentially activated in dividing cells; promoters which respond to a stimulus such as steroid hormone receptor (Cicatiello et al., 1995) and retinoic acid receptor (Mendelsohn et al., 1994) promoters; tetracycline-regulated transcriptional modulators (Furth et al., 1994); cytomegalovirus immediate-early; retroviral LTR (Choate et al., 1996), metallothionein; SV-40; E1a and MLP promoters. Tetracycline-regulated transcriptional modulators and CMV promoters are described in WO 96/01313, U.S. Pat. Nos. 5,168,062 and 5,385,839, the contents of which are incorporated herein by reference.

Vectors

As discussed above, a "vector" is any means for the transfer of a nucleic acid into a host cell. Preferred vectors are plasmids and viral vectors, such as retroviruses.

Viral vectors may be used to produce a transgenic animal according to the invention. Preferably, the viral vectors are replication defective, that is, they are unable to replicate autonomously in the target cell. In general, the genome of the replication defective viral vectors which are used within the scope of the present invention lack at least one region which is necessary for the replication of the virus in the infected cell. These regions can either be eliminated (in whole or in part), be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (on the isolated DNA) or in situ, using the techniques of genetic manipulation or by treatment with mutagenic agents.

Preferably, the replication defective virus retains the sequences of its genome which are necessary for encapsidating the viral particles.

The retroviruses are integrating viruses which infect dividing cells. The retrovirus genome includes two LTRs, an encapsidation sequence and three coding regions (gag, pol and env). The construction of recombinant retroviral vectors has been described: see, in particular, EP 453242, EP178220, Bernstein et al. Genet. Eng. 7 (1985) 235; McCormick, BioTechnology 3 (1985) 689, etc. In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are disclosed in WO95/02697.

In general, in order to construct recombinant retroviruses containing a nucleic acid sequence, a plasmid is constructed which contains the LTRs, the encapsidation sequence and the coding sequence. This construct is used to transfect a packaging cell line, which cell line is able to supply in trans the retroviral functions which are deficient in the plasmid. In general, the packaging cell lines are thus able to express the gag, pol and env genes. Such packaging cell lines have been described in the prior art, in particular the cell line PA317 (U.S. Pat. No. 4,861,719); the PsiCRIP cell line (WO90/02806) and the GP+envAm-12 cell line (WO89/07150). In addition, the recombinant retroviral vectors can contain modifications within the LTRs for suppressing transcriptional activity as well as extensive encapsidation sequences which may include a part of the gag gene (Bender et al., J. Virol. 61 (1987) 1639). Recombinant retroviral vectors are purified by standard techniques known to those having ordinary skill in the art.

Drug Screening Assays

Transgenic animals overexpressing a MDM2 gene are useful in drug screening assays. These assays are useful for identifying compounds effective for the treatment of diseases, such as diseases of the skin or respiratory tract. Preferred diseases include ichthyosis, psoriasis, tumors, asthma, eczema, and allergic rhynitis.

The drug screening assays of the invention may be performed on a large scale or small scale. Large scale screening involves visual observation of the skin, or other tissue overexpressing a MDM2 gene, and comparison to control animals. For example, if the skin of the transgenic animal over-expresses a MDM2 gene, a scaly "fish-skin" appearance characteristic of ichthyosis vulgaris is readily apparent. The observer would evaluate a drug candidate based on its ability to decrease this scaly "fish-skin" appearance relative to untreated animals.

Large scale tests could also be automated to screen drug candidates based on light reflectance/absorbance of localized areas of the skin of immobilized animals. The skin of young animals from birth until the hair grows (10 days) is normally shiny and transparent. Drug candidates could be evaluated for their ability to produce a more normal skin appearance, such as measured by reflectance or absorbance, in transgenic animals of ichthyosis.

Alternatively, transgenic animals overexpressing a MDM2 gene and also comprising a reporter gene operably linked to a skin promoter whose expression is altered by MDM2, may be prepared. For example, a K14 promoter operably linked to GFP would display differential fluorescence depending on the presence or absence of corrective treatment.

Drug screening assays of the invention can also be performed on a small scale. Small scale assays involve biopsy and either histological and/or immunohistochemical analyses. Ichthyosis vulgaris is characterized by epidermal hyperproliferation, lack of production of keratohyalin granules, and hyperkeratosis, exemplified by the cornified layer containing an excess of incompletely differentiated corneocytes and a defective barrier function. The thickness of the epidermis is strikingly altered, as well as the aspect of the cornified/transition layer. These characteristics can be evaluated histologically by a skilled practioner. Immunohistochemical analysis can be performed using K14 as a marker.

Treatment of Skin Diseases

The present invention provides a method for modulating MDM2 function in a cell by administering to the cell a compound capable of modulating MDM2 levels and/or biological activity within the cell. In a preferred aspect of the invention the cells are cells of a patient suffering from a disease of the skin or respiratory tract, and the method comprises administering to the cells of a patient a compound capable of modulating MDM2 function. Such diseases include ichthyosis, psoriasis, tumors, asthma, eczema, and allergic rhynitis.

Compounds capable of modulating MDM2 function include those that are capable of inhibiting or down-regulating MDM2 gene expression or of inhibiting the biological activity of MDM2 in a cell. Such compounds include antisense nucleic acids, intracellular binding proteins and any compound identified using the transgenic animals and assays described herein.

Preparation and use of antisense polynucleotides, DNA encoding antisense RNA molecules and use of oligo and genetic antisense is disclosed in WO 92/15680, the entire contents of which are incorporated herein by reference. Antisense nucleic acids for use according to the invention are preferably RNA capable of specifically hybridizing with all or part of a MDM2 gene, or its corresponding messenger RNA. The antisense sequence may be derived from DNA sequences whose expression in the cell produces RNA complementary to all or part of a MDM2 gene. These antisense sequences can be prepared by expression of all or part of a sequence encoding MDM2 in the opposite orientation (EP 140 308). Any length of the antisense sequence is suitable for practice of the invention so long as it is capable of down-regulating or blocking expression of a MDM2 gene. Preferably, the antisense sequence is at least 20 nucleotides in length.

In one aspect the nucleic acid encodes antisense RNA molecules. In this embodiment, the nucleic acid is operably linked to suitable regulatory regions (discussed above) enabling expression of the nucleic acid sequence, and is introduced into a cell utilizing, preferably, recombinant vector constructs, which will express the antisense nucleic acid once the vector is introduced into the cell. Examples of suitable vectors includes plasmids, adenoviruses, adeno-associated viruses (see WO 91/18088; WO 93/09239; U.S. Pat. No. 4,797,368, U.S. Pat. No. 5,139,941, EP 488 528), retroviruses (see above), and herpes viruses. For delivery of a therapeutic gene the vector is preferably an adenovirus. Adenoviruses are eukaryotic DNA viruses that can be modified to efficiently deliver a nucleic acid of the invention to a variety of cell types.

Various serotypes of adenovirus exist. Of these serotypes, preference is given, within the scope of the present invention, to using type 2 or type 5 human adenoviruses (Ad 2 or Ad 5) or adenoviruses of animal origin (see WO94/26914). Those adenoviruses of animal origin which can be used within the scope of the present invention include adenoviruses of canine, bovine, murine (example: Mav1, Beard et al., 1990), ovine, porcine, avian, and simian (example: SAV) origin. Preferably, the adenovirus of animal origin is a canine adenovirus, more preferably a CAV2 adenovirus (e.g. Manhattan or A26/61 strain (ATCC VR-800), for example).

Preferably, the replication defective adenoviral vectors of the invention comprise the ITRs, an encapsidation sequence and the nucleic acid of interest. Still more preferably, at least the E1 region of the adenoviral vector is nonfunctional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (WO95/02697), the E2 region (WO94/28938), the E4 region (WO94/28152, WO94/12649 and WO95/02697), or in any of the late genes L1–L5.

In a preferred embodiment, the adenoviral vector has a deletion in the E1 region (Ad 1.0). Examples of E1-deleted adenoviruses are disclosed in EP 185,573, the contents of which are incorporated herein by reference. In another preferred embodiment, the adenoviral vector has a deletion in the E1 and E4 regions (Ad 3.0). Examples of E1/E4-deleted adenoviruses are disclosed in WO95/02697 and WO96/22378, the contents of which are incorporated herein by reference. In still another preferred embodiment, the adenoviral vector has a deletion in the E1 region into which the E4 region and the nucleic acid sequence are inserted (see FR94 13355, the contents of which are incorporated herein by reference).

The replication defective recombinant adenoviruses according to the invention can be prepared by any technique known to the person skilled in the art (Levrero et al., 1991; EP 185 573; Graham, 1984). In particular, they can be prepared by homologous recombination between an adenovirus and a plasmid which carries, inter alia, the DNA sequence of interest. The homologous recombination is effected following cotransfection of the said adenovirus and plasmid into an appropriate cell line. The cell line which is employed should preferably (i) be transformable by the said elements, and (ii) contain the sequences which are able to complement the part of the genome of the replication defective adenovirus, preferably in integrated form in order to avoid the risks of recombination. Examples of cell lines which may be used are the human embryonic kidney cell line 293 (Graham et al., 1977) which contains the left-hand portion of the genome of an Ad5 adenovirus (12%) integrated into its genome, and cell lines which are able to complement the E1 and E4 functions, as described in applications WO94/26914 and WO95/02697. Recombinant adenoviruses are recovered and purified using standard molecular biological techniques, which are well known to one of ordinary skill in the art.

Another embodiment of the present invention's method of specifically inhibiting MDM2 activity at selected sites such as in the skin, comprises inhibiting MDM2 function by expression of a nucleic acid sequence encoding an intracellular binding protein capable of selectively interacting with MDM2 within a transfected cell. WO 94/29446 and WO 94/02610, the entire contents of which are incorporated herein by reference, disclose cellular transfection with genes encoding an intracellular binding protein. An intracellular binding protein includes any protein capable of selectively interacting, or binding, with MDM2, including human MDM2, in the cell in which it is expressed and of neutralizing the function of bound MDM2. Preferably, the intracellular binding protein is an antibody or a fragment of an antibody. Preferably, the intracellular binding protein is a single chain antibody.

WO 94/02610 discloses preparation of antibodies and identification of the nucleic acid encoding a particular antibody. Using MDM2 protein or a fragment thereof, a monoclonal antibody specific for MDM2 is prepared according to techniques known to those skilled in the art. A vector comprising the nucleic acid encoding an intracellular binding protein, or a portion thereof, and capable of expression in a host cell is subsequently prepared for use in the method of this invention. Suitable vectors and methods of delivering nucleic acids encoding intracellular binding proteins to cells containing MDM2 include those discussed above for delivery of antisense nucleic acids.

In a preferred aspect of this embodiment, the nucleic acid sequence encoding a MDM2 intracellular binding protein additionally comprises a sequence encoding a localization signal for targeting the intracellular binding protein to the cellular location of MDM2 and/or a sequence enabling insertion of the intracellular binding protein in the plasma membrane. The localization signal or insertion sequence can be located anywhere on the intracellular binding protein, so long as it does not interfere with binding to MDM2. Examples of localization signals are disclosed in WO 94/02610.

Pharmaceutical Compositions

Compounds capable of modulating MDM2 function, include antisense nucleic acids, intracellular binding proteins and compounds identified using the transgenic animals and assays described herein.

Antisense nucleic acid constructs are capable of down-regulating or blocking expression of a MDM2 gene, and may be delivered locally to cells of the skin, such as in the form of a cream or lotion. The nucleic acids, either in the form of a vector or naked DNA, may be combined with one or more pharmaceutically acceptable carriers for an injectable formulation. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilised water or physiological saline, allow the constitution of injectable solutions.

The preferred sterile injectable preparations can be a solution or suspension in a nontoxic parenterally acceptable solvent or diluent. Examples of pharmaceutically acceptable carriers are saline, buffered saline, isotonic saline (e.g. monosodium or disodium phosphate, sodium, potassium, calcium or magnesium chloride, or mixtures of such salts), Ringer's solution, dextrose, water, sterile water, glycerol, ethanol, and combinations thereof. 1,3-butanediol and sterile fixed oils are conveniently employed as solvents or suspending media. Any bland fixed oil can be employed including synthetic mono- or di-glycerides. Fatty acids such as oleic acid also find use in the preparation of injectables.

If administered as a virus the dose(s) may be adapted as a function of various parameters, and in particular as a function of the site (skin) of administration considered, the number of injections, the gene to be expressed or alternatively the desired duration of treatment. In general, recombinant adenoviruses are formulated and administered in the form of doses of between $10^4$ and $10^{14}$ pfu, and preferably $10^6$ to $10^{11}$ pfu. The term pfu (plaque forming unit) corresponds to the infectivity of a virus solution, and is determined by infecting an appropriate cell culture and measuring, generally after 15 days, the number of plaques of infected cells. The technique for determining the pfu titre of a viral solution are well documented in the literature.

A nucleic acid, such as that encoding an antisense or intracellular binding protein, can also be administered as a naked DNA. Methods for formulating and administering naked DNA to mammalian muscle tissue are disclosed in U.S. Pat. Nos. 5,580,859 and 5,589,466, the contents of which are incorporated herein by reference.

EXAMPLES

The present invention will be described in greater detail with the aid of the following examples which should be considered as illustrative and nonlimiting.

General Molecular Biology

The techniques of recombinant DNA technology are known to those of ordinary skill in the art. General methods for the cloning and expression of recombinant molecules are described in Maniatis (*Molecular Cloning*, Cold Spring Harbor Laboratories, 1982), and in Ausubel (*Current Protocols in Molecular Biology*, Wiley and Sons, 1987), which are incorporated by reference.

EXAMPLE I

Construction of Transgenic Mice Overexpressing MDM2

Construction of the HCMV/MDM2 Expression Vector:

The MDM2 construct was prepared from a mouse cDNA clone obtained from a mouse testis library (Stratagene). This cDNA has three amino acid changes compared to the original sequence published by Fakharzadeh et al. (1991) (203 T to S, 419 H to D and 486 S to T). The 5' end of the cDNA was modified to improve the efficiency of translation by introducing a Kozak sequence and a β globin leader sequence. This results in a change of the second amino acid of MDM2, a substitution of a glycine for a cysteine residue.

Figures 1A, 1B:
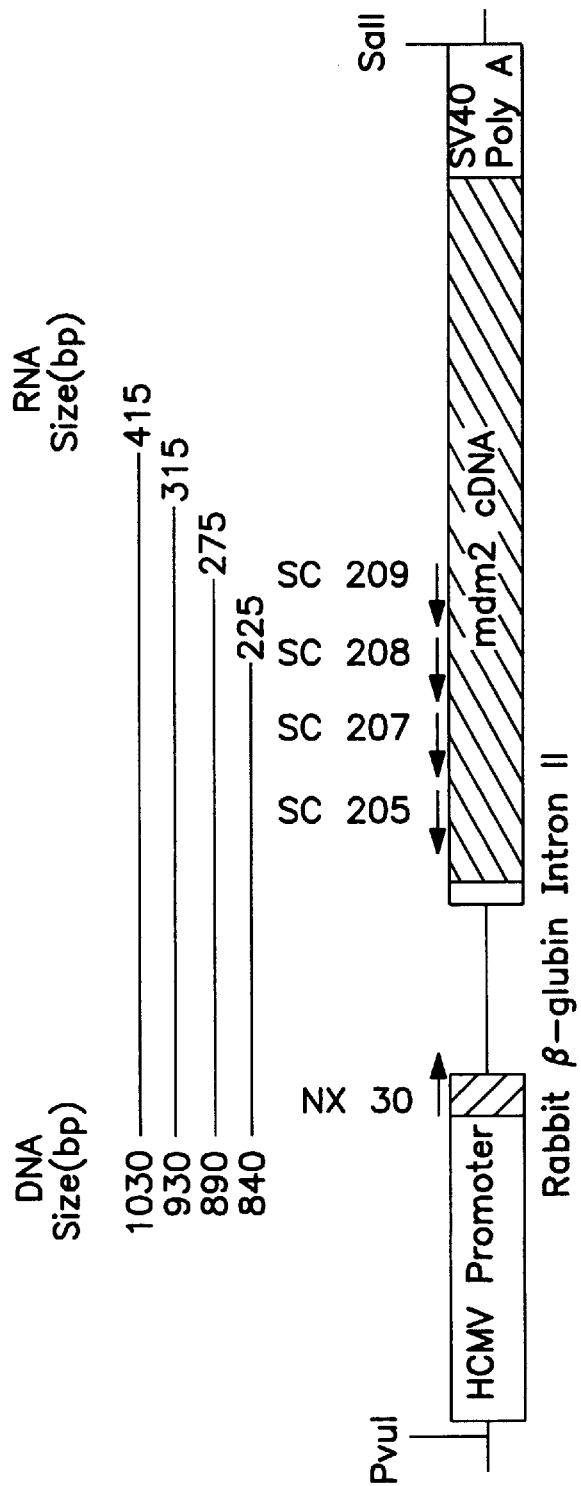
FIGS. 1(A and B): Transgene construct and HCMV/MDM2 transgenic lines.
Figure 2A:
Figure 2B:
Figure 2C:
Figure 2D:

A 1470 bp fragment coding for MDM2 was generated by PCR (sense primer: 5'-GCCATGGGCAATACCAACATGTC-3' (SEQ ID NO:1), antisense primer: 5'-GACTAGTGGTCAGCTAGTTGAAG-3' (SEQ ID NO:2); PCR conditions: 7 min. at 90° C. then 25 cycles, 1 min at 93° C., 2 min at 55° C. and 3 min at 72° C.), digested with Nco1 and Spe1 and cloned downstream from the 60 nucleotides 5' leader of the B-globin cDNA in pT7SAP1B. The resulting recombinant was digested with HindIII and Spe1 and the β-globin-MDM2 sequence was cloned in the pBKCMV vector (Stratagene) that had been digested with XhoI, repaired and then digested with HindIII. The HindIII/Kpn1 fragment, containing the modified MDM2 sequence, was cloned in PXJ41 (Xiao et al. 1991), to give pCMV/MDM2 (FIG. 1).

Production of Transgenic Mice:

In order to purify the CMV/MDM2 transcription unit, pCMV/MDM2 was digested with Pvu1 and Sal1, the 3,000 bp fragment was purified using the Gene Clean spin kit followed by an Elutip column and dissolved in 10 mM Tris-HCl PH 7.5, 0.25 mM EDTA. The DNA (2 micogram/ml) was microinjected into the pronuclei of fertilized oocyctes obtained from superovulated F1 females from a cross between SJL male and C57/BL6 females. Eggs that survived microinjections were implanted into the oviduct of pseudopregnant (CD1) foster females.

Tail DNA was analysed by Southern blotting and PCR (primers: sense, 5'-ACTCTTTTGAAGGAGATCCT-3' (SEQ ID NO:3); antisense: 5'-CCATCAGGCACATCCAAGCC-3') (SEQ ID NO:4) to identify transgenic mice. The founders and their progeny were bred by back-crossing to C57BL/6 mice, generating mice that were hemizygous for the transgene. The transgene is expressed in three of the lines (HCMV5, HCMV21, HCMV25) in all of the progeny. Two transgenic lines (HCMV19, HCMV20), that do not express the transgene, were used as controls.

Histological and Ultrastructural Analysis:

Skin samples were fixed by immersion in 2.5% glutaraldehyde in 0.1 M cacodylate buffer pH 7.2 overnight at room temperature, washed in cacodylate buffer for a further 30 minutes followed by post-fixation with 1% osmium tetroxide in 0.1 M cacodylate buffer for 1 hour at 4° C. Tissues were dehydrated through graded alcohol (50, 70, 90 and 100%) for 30 minutes each and embedded in Epon 812. Semi-thin1.5 mm sections were cut and stained with toluidine blue and analysed histologically by light microscopy. Ultra-thin 70 nm section were cut, stained with uranyl acetate and lead citrate and examined with a Philips 208 electron microscopy. For scanning electron microscopy, skin samples were fixed, dehydrated as above, dried with a critical point drying apparatus and mounted in aluminum stubs coated with palladium-gold using a cold sputter-coater and observed with a Philips XL-20 microscope.

Immunodetection of MDM2 and Skin Marker Proteins:

For immuno-histochemistry, skin samples were fixed with 4% paraformaldehyde and embedded in paraffin. Six mm thick tissue sections were de-paraffinized and incubated with rabbit polyclonal antibodies to MDM2 (generously provided by T. Léveillard), Loricrin and Involucrin (Medatom Europa), Cytokeratines 1, 10,14 and Filaggrin. They were then incubated with Biotin-conjugated anti-rabbit IgG (Jackson laboratory) diluted 1/200 with PBS containing 1% dry milk for 30 minutes at room temperature and then the signal was detected using the Histomouse SP kit (Zymed Laboratory). The sections were examined with a microscope. Controls contained biotin-conjugated anti-rabbit IgG alone.

For western immunoblots, skin samples were homogenized with RIPA buffer using an UltraThorax homogenizer. Equal amounts of protein were loaded on 10% SDS polyacrylamide gels, electrophoresed and transfered onto nitrocellulose membranes. The blots were incubated with MDM2 antibodies for 1 hour, followed by peroxidase-conjugated anti-rabbit IgG (Jackson laboratory) diluted 1/2000.

Apoptosis Assay:

We used the TUNEL procedure (Gorczyca, W. et al., 1993), in which terminal deoxynucleotidyl transferase (TdT) incorporates fluorescein-labelled nucleotides at double or single strand breaks in DNA from cells undergoing apoptosis. Briefly, six mm thick tissue sections were deparaffinized and rehydrated, incubated for 10 minutes at room temperature in permeabilisation solution (0.1% Triton-X-100 in 0.1% (w/v) sodium citrate) and treated with TdT (Biovation, UK) according to the manufacturer's instructions. Labeled nuclei were visualized directly by fluorescence microscopy with filters to detect fluorescein (FITC). Apoptotic nuclei have a bright green fluorescence.

BrdU Labelling and Detection:

To label cells in S phase, mice were injected under the skin with 1 ml concentrated BrdU (Zymed) per 100 g body weight and sacrificed 2 hours later (Kim SH et al 1993). Skin samples were fixed with 4% formaldehyde in PBS and embedded in paraffin. Six micrometer sections were treated with a biotinylated-monoclonal antibody against BrdU (Zymed) and positive nuclei were detected according to the manufacturer's instructions.

p53 Knock-Out Mice:

p53-null mice were obtained from Jackson Laboratory. The genotype of the progeny obtained by crossing the p53-null mice with MDM2 transgenic mice was determined by PCR. To distinguish between the wild-type and recombined copies of p53, a mixture of three primers was used: two sense primers, from exon 6 of p53 (5'-ACAGCGTGGTGGTACCTTAT-3') (SEQ ID NO:5) and the neomycin gene (5'-TCCTCGTGCTTTACGGTATC-3') (SEQ ID NO:6) and an antisense primer from exon 7 of p53 (5'-TATACTCAGAGCCGGCCT-3') (SEQ ID NO:7).

Results and Discussion

Several transgenic mice lines overexpressing a MDM2 gene under the control of the HCMV promoter have been generated. At the RNA level, transgene expression was shown to be highest in the skin followed by the abdominal wall, tongue, eyes, muscle, kidney, intestine, lung and stomach, respectively. At the protein level, with a rabbit polyclonal antibody raised against MDM2, we detected the highest levels of transgene expression in the skin, with lower levels in the thymus, lung, kidney, liver and brain. The level of expression varied from one line to another with the highest level of expression in HCMV25 followed by HCMV21, HCMV20 and HCMV5 (FIG. 1). In all lines the skin phenotype showed different levels of severity, which correlated with the level of expression of the transgene. Line HCMV25 with the highest level of transgene expression, displays post-natal lethality. The cause of lethality is not known. However, it is partially rescued by crossing the HCMV25 line (B6 background) with p53+/+ (SV129 background). Analysis of the different combinations HCMV25/p53−/−, HCMV25/p53−/+ or HCMV25/p53+/+ indicated that the rescue of the lethal phenotype was not due to p53 status.

In the skin, the transgene is mainly expressed in the granular layer with moderate expression in the hair follicles (FIG. 6). The phenotype of the HCMV-MDM2 mice resembles ichthyosis vulgaris characterized by a scaly "fish-skin" appearance with abnormal desquamation (FIG. 2). Histopathology of skin from transgenic mice revealed a striking abnormality in the epidermis. It is unusually thick, and cell size and organization within the basal layer are perturbed (FIG. 4.). The cornfield layer contains an excess of incompletely differentiated corneocytes and takes up more stain, possibly due to a defective barrier function (FIG. 4, see composition and density of staining of the cornified layer). The granular layer in transgenic mice is thicker compared to control mice with a marked decrease in the number of keratohyalin granules (FIG. 4). These observations were further confirmed by ultra structural studies using electron microscopy (FIG. 5). The thickness of the epidermis in transgenic skin is due to increased level of proliferation as shown in (FIG. 7). BrdU incorporation is localized in the basal layer, where the transgene is not highly expressed. It is not known whether the increased level of proliferation in the basal layer is due to MDM2 over-expression or to a homeostatic effect induced by altered skin differentiation.

Figure 7A:
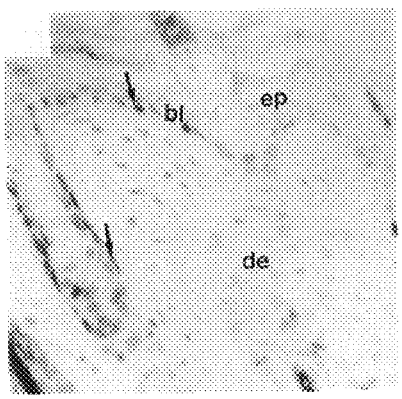
Figure 7C:
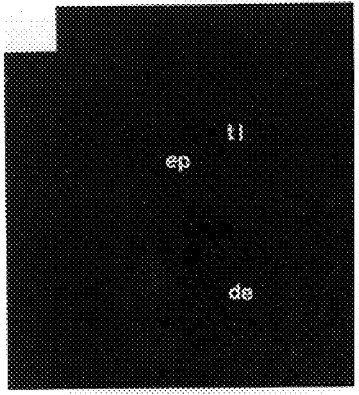
Figure 7E:
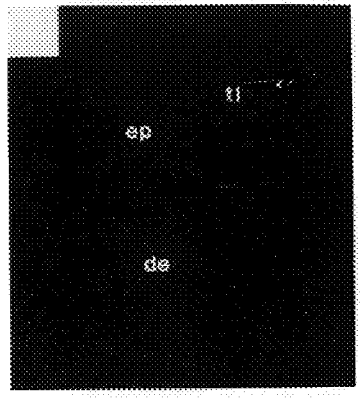
Figure 7B:
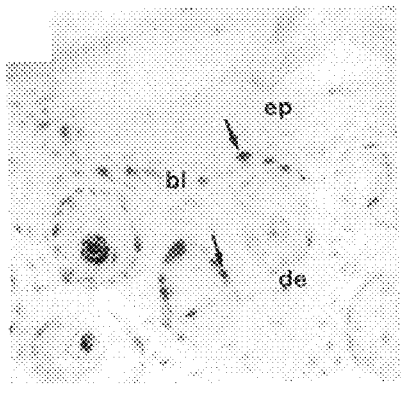
Figure 7D:
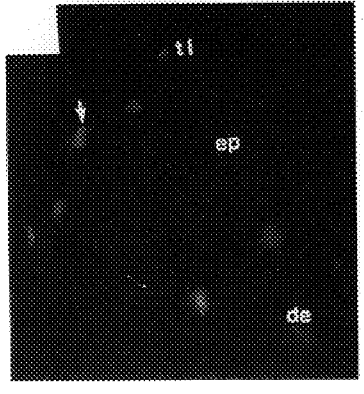
Figure 7F:
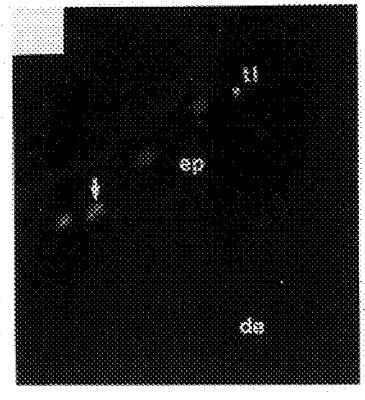

Interestingly, an increase in apoptosis by the TUNEL method was detected in the layer where the MDM2 transgene is highly expressed (see FIG. 6B for MDM2 expression and FIG. 7D,F for apoptosis). Induction of apoptosis by MDM2 is p53-independent since it was detected on p53−/− (FIG. 7F) and p53+/+ (FIG. 7D) backgrounds. In addition, the overexpression of MDM2 in p53−/− mice does not accelerate tumor formation (data not shown). This points to MDM2 being able to induce apoptosis in vivo. The most striking effect of MDM2 is the inducing of the scaly "fish skin" (FIG. 2) which is found in the human skin disease, ichthyosis (this effect is p53-independant, see FIG. 3). By immunohistochemical studies, using several skin differentiation marker antibodies, the inventors have shown that cells with high level of transgene expression are less differentiated as shown by the absence or reduction in expression of terminal skin differentiation markers such as loricrin, involucrin and filaggrin. In addition, the "granular layer" in transgenic skin continues to express cytokeratin 14 which is usually turned off when cells migrate to the granular layer (FIG. 8). MDM2 may directly inhibit transactivation of such skin markers, as it does for p53, or it may inhibit indirectly by interacting with other factors.

Conclusion

A murine MDM2 under the control of a strong ubiquitous HCMV promoter has been introduced into transgenic mice. Five lines expressing different levels of MDM2 have been generated. Over-expression of MDM2 decreases the viability of the mice and does not accelerate tumor formation. Strikingly, these mice showed an abnormal skin phenotype resembling ichthyosis and this phenotype was observed on both p53 wild type and null backgrounds. Histopathological examination of transgenic mouse skin showed that they had a thicker epidermis when compared to wild type mice. MDM2 was found to be overexpressed in the granular layer of the epidermis. A decrease in the number and size of the keratohyaline granules within the thicker "granular layer" in MDM2 transgenic mice has been observed by electron microscopy. Several skin differentiation markers were found to be deregulated. In transgenic mice, cytokeratin 14 was found to be expressed, Filaggrin and involucrine were somewhat decreased in the granular layer. With the TUNNEL assay the inventors found that the granular cells showed active apoptosis on both p53 wild type and null backgrounds. These results demonstrate that MDM2 can affect skin differentiation and induce apoptosis independently of p53.

All the references discussed herein are incorporated by reference.

One skilled in the art will readily appreciate the present invention is well adapted to carry out the objects and obtain the ends and advantages mentioned, as well as those inherent therein. The transgenic animals, methods, procedures and techniques described herein are presented as representative of the preferred embodiments, and intended to be exemplary and not intended as limitations on the scope of the present invention. Changes therein and other uses will occur to those of skill in the art which are encompassed within the spirit of the invention or defined by the scope of the appended claims.

REFERENCES CITED

Austin S J; Fujimoto W; Marvin K W; Vollberg T M; Lorand L; Jetten A M (1996): Cloning and regulation of cornifin beta, a new member of the cornifin/spr family. Suppression by retinoic acid receptor-selective retinoids. *J Biol Chem*, 271(7) p3737–42.

Barak, Y. and Oren, M. (1992) Enhanced binding of a 95 kDa protein to p53 in cells undergoing p53 mediated growth arrest. *EMBO J.*, 11, 2115–2121.

Beard et al., (1990) Virology 75, 81.

Bradley, A., et al. (1984) *Nature* 309, 255–258.

Brinster, et al., (1985) *Proc. Natl. Acad. Sci. USA* 82, 4438–4442

Bronson S K; Plaehn E G; Kluckman K D; Hagaman J R; Maeda N; Smithies O (1996): Single-copy transgenic mice with chosen-site integration. *Proc Natl Acad Sci USA*, 93(17) p9067–9072.

Cahilly-Snyder, L., Yang-Feng, T., Francke,U. and George, D. L. (1987) Molecular analysis and chromosomal mapping of amplified genes isolated from a transformed mouse 3T3 cell line. *Somatic Cell Mol. Genet.*, 13, 235–244.

Carroll J M; Romero M R; Watt F M (1995): Suprabasal integrin expression in the epidermis of transgenic mice results in developmental defects and a phenotype resembling psoriasis. *Cell*, 83(6) p957–68.

Carroll J M, Crompton T, Seery J P, Watt F M (1997): Transgenic mice expressing IFN-gamma in the epidermis have eczema, hair hypopigmentation, and hair loss. *J Invest Dermatol* 108 (4): 412–422.

Cicatiello L; Cobellis G; Addeo R; Papa M; Altucci L; Sica V; Bresciani F; Le Meur M; Kumar V L; Chambon P; et al (1995): In vivo functional analysis of the mouse estrogen receptor gene promoter: a transgenic mouse model to study tissue-specific and developmental regulation of estrogen receptor gene transcription. *Mol Endocrinol*, 9: p1077–1090.

Chen, J., Marechal, V. and Levine, A. J. (1993) Mapping of the p53 and mdm-2 interaction domains. *Mol. Cell. Biol.*, 13, 4107–4114.

Chen, J., Wu, X., Lin, J. and Levine, A. J. (1996) mdm-2 inhibits the G1 arrest and apoptosis functions of the p53 tumor suppressor protein. *Mol. Cell. E'iol.*, 16, 2445–2452.

Choate K A, Kinsella T M, Williams M L, Nolan G P, Khavari P A (1996):
Transglutaminase 1 delivery to lamellar ichthyosis keratinocytes. *Hum Gene Ther* 7 (18): 2247–2253.

Cordon-Cardo, C., Latres, E., Drobnjak, M., Oliva, M. R., Pollack, D., Woodruff, J. M., Marechal, V., Chen, J., Brennan, M. F. and Levine A. J. (1993) Molecular abnormalities of MDM2 and p53 genes in adult soft tissue sarcomas. *Cancer Res.*, 54, 794–799.

Dubs-Poterszman, M. C., Tocque, B. and Wasylyk, B. (1995). MDM2 transformation in the absence of p53 and abrogation of the p107 G1 cell-cycle arrest. Oncogenes, 11, 2445–2449.

Epstein, E. H., (1996) *Current Opinion in Genetics and Development* 6, 295–300.

Evans, M. J., et al., (1981) *Nature* 292, 154–156.

Fakharzadeh, S. S., Trusko, S. P. and George D. L. (1991) Tumorigenic potential associated with enhanced expression of a gene that is amplified in a mouse tumor cell line. *EMBO J.*, 10, 1565–1569.

Feng X, Peng Z H, Di W, Li X Y, Rochette-Egly C, Chambon P, Voorhees J J, Xiao J H (Jan 1 1997): Suprabasal expression of a dominant-negative RXR alpha mutant in transgenic mouse epidermis impairs regulation of gene transcription and basal keratinocyte proliferation by RAR selective retinoids. *Genes Dev* 11 (1): 59–71.

Fiddler, T. A., Smith, L., Tapscott, S. J., and Thayer M. J. (1996). Amplification of MDM2 inhibits MyoD-mediated myogenesis. *Mol. Cell. Biol.*, 16, 5048–5057.

Finlay, C. (1993) The mdm-2 oncogene can overcome wild-type p53 suppression of transformed cell growth. *Mol. Cell. Biol.*, 13, 301–306.

Furth P A; St Onge L; Boger H; Gruss P; Gossen M; Kistner A; Bujard H; Hennighausen (1994): Temporal control of gene expression in transgenic mice by a tetracycline-responsive promoter. *Proc Natl Acad Sci*, 91(20) p9302–9306.

Galou M; Pournin S; Ensergueix D; Ridet J L; Tchelingerian J L; Lossouarn L; Privat A; Babinet C; Dupouey P, Lossouarn L; Privat A; Babinet C; Dupouey P (1994): Normal and pathological expression of GFAP promoter elements in transgenic mice. *Glia*, 12(4) p281–293.

Gloster A; Wu W; Speelman A; Weiss S; Causing C; Pozniak C; Reynolds B; Chang E; Toma J G; Miller F D (1994): The T alpha 1 alpha-tubulin promoter specifies gene expression as a function of neuronal growth and regeneration in transgenic mice. *J Neurosci*, 14(12) p7319–30.

Gorczyca, W., Gong J. and Darzynkiewiez, Z., 1993, Cancer Research 53: 1945–1951.

Gossler, et al., (1986) *Proc. Natl. Acad. Sci. USA* 83, 9065–9060.

Graham et al., (1977) J. Gen. Virol. 36, 59.

Graham, (1984) EMBO J. 3, 2917.

Haines, D. S., Landers, J. E., Engle, L. J. and George, D. L. (1994) Physical and functional interaction between wild-type p53 and mdm-2 proteins. *Mol. Cell. Biol.*, 14, 1171–1178.

Haupt, Y., Barak, Y. and Oren, M. (1996) Cell type specific inhibition of p53-mediated apoptosis by MDM2. *EMBO J.*, 15, 1596–1 606.

Hogan et al., (1986) in Manipulating the Mouse Embryo, Cold Spring Harbor Laboratory Press, Cold Spring Harbor, N.Y.

Hsu-Wong S; Katchman S D; Ledo I; Wu M; Khillan J; Bashir M M; Rosenbloom J; Uitto J (1994): Tissue-specific and developmentally regulated expression of human elastin promoter activity in transgenic mice. *J Biol Chem*, 269(27) 18072–18075.

Jaenich, R. (1976) *Proc. Natl. Acad. Sci. USA* 73, 1260–1264.

Jaenisch, R. (1988) *Science* 240, 1468–1474.

Jahner et al., (1982) *Nature* 298:623–628.

Jahner et al., (1985) *Proc. Natl. Acad. Sci. USA* 82, 6927–6931.

Johnson, L. D., Idler, W. W., Zhou, X. M., Roop, D. R. and Steinert, P. M.(1985): Structure of a gene for the human epidermal 67-kDa keratin. *Proc. Natl. Acad. Sci. U.S.A.* 82 (7), 1896–1900.

Jones, S. N., Roe, A. E., Donehower, L. A. and Bradley, A. (1995). Rescue of embryonic lethality in Mdm2-deficient mice by absence of p53. *Nature*, 378, 2(16–208.

Leach, F. S., Tokino, T., Meltzer, P., Burrell, M., Oliner, J. B., Smith, S., Hill, D. E., Sidransky, D., Kinzler, K. W. and Vogelstein, B. (1993) p53 mutation and MDM2 amplification in human soft tissue sarcomas. Cancer Res., 53, 2231–2234.

Lee K K; Webb S E; Cai D Q; Sze L Y; Lam K H; Li Z; Paulin D (1995):
Desmin transgene expression in mouse somites requires the presence of the neural tube. *Int J Dev Biol*, 39(3) p469–75.

Lee J H; Jang S I; Yang J M; Markova N G; Steinert P M (1996): The proximal promoter of the human transglutaminase 3 gene. Stratified squamous epithelial-specific expression in cultured cells is mediated by binding of Sp1 and ets transcription factors to a proximal promoter element. *J Biol Chem*, 271(8) p4561–8.

Levrero et al., (1991) Gene 101, 195.

Matthews R P; McKnight G S (1996): Characterization of the cAMP response element of the cystic fibrosis transmembrane conductance regulator gene promoter. *J Biol Chem*, 271(50) p31869–77.

McGlynn L K; Mueller C R; Begbie M; Notley C R; Lillicrap D (1996):
Role of the liver-enriched transcription factor hepatocyte nuclear factor 1 in transcriptional regulation of the factor Viii gene. *Mol Cell Biol* (United States), 16(5) pl936–45.

Mendelsohn C; Larkin S; Mark M; Le Meur M; Clifford J; Zelent A; Chambon P (1994): RAR beta isoforms distinct transcriptional control by retinoic acid and specific spatial patterns of promoter activity during mouse embryonic development. *Mech Dev*, 45(3) p227–241.

Missero C, Serra C, Stenn K, Dotto GP (1993): Skin-specific expression of a truncated E1a oncoprotein binding to p105-Rb leads to abnormal hair follicle maturation without increased epidermal proliferation. *J Cell Biol* 121 (5): 1109–1120

Momand, J., Zambetti, G. P., Olson, D. C., Gorge, D. and Levine A. J. (1992) The mdm-2 oncogene product forms a complex with the p53 protein ard inhibits p53-meditated transactivation. Cell, 69, 1237–1245.

Montes de Oca Luna, R., Wagner, D. S. and Lozano, G. (1995). Rescue of early embryonic lethality in MDM2-deficient mice by deletion of p53. *Nature*, 378, 203–206.

Oliner, J. D., Kinzler, K. W., Meltzer, P. S., George, D. L. and Vogelstein, B. (1992) Amplification of a gene encoding a p53-associated protein in human sarcomas. *Nature*, 358, 80–83.

Oliner, J. D., Pietenpol, J. A. Thiagalingam, S., Gyuris, J., K inzler, K. W. and Vogelstein, B. (1993). Oncoprotein MDM2 conceals the activation domain of tumor suppressor p53. *Nature*, 362, 857–860.

Ray M K; Chen C Y; Schwartz R J; De Mayo F J (1996): Transcriptional regulation of a mouse Clara cell-specific protein (mCC10) gene by the Nkx transcription factor family members thyroid transcription factor 1 and cardiac muscle-specific homeobox protein (CSX). *Mol Cell Biol*, 16(5) p2056–64.

Rincon-Limas D E; Geske R S; Xue J J; Hsu C Y; Overbeek P A; Patel P I (1994): 5'-flanking sequences of the human HPRT gene direct neuronal expression in the brain of transgenic mice. *J Neurosci Res*, 38(3) p259–67.

Robertson, et al., (1986) *Nature* 322, 445–448.

Sigalas, I., Calvert, A. H., Anderson, J. J., Neal, D. E., and 1 unec, J., (1996) Alternatively spliced MDM2 transcripts with loss of p53 binding domain sequences: transforming ability and frequent detection in human cancer. *Nature Medecine*, 2, 912–917.

Stewart et al., (1987) EMBO J. 6:383–388.

Van der Putten et al., (1985) *Proc. Natl. Acad. Sci. USA* 82, 6148–6152.

Vicart P; Schwartz B; Vandewalle A; Bens M; Delouis C; Panthier J J; Pournin S; Babinet C; Paulin D (1994): Immortalization of multiple cell types from transgenic mice using a transgene containing the vimentin promoter and a conditional oncogene. *Exp Cell Res*, 214(1) p35–45.

Wang X, Zinkel S, Polonsky K, Fuchs E (1997): Transgenic studies with a keratin promoter-driven growth hormone transgene: prospects for gene therapy. *Proc Natl Acad Sci USA* 94 (1): 219–226.

Williams, M. L. (1992) Pediatric Dermatology 9, 365–368.

Wu, X., Bayle, J. H., Olson, D. and Levine, A. J. (1993) The p53-mdm-2 autoregulatory feedback loop. *Genes Dev.*, 7, 1126–1132.

Xiao et al. 1991, Cell 65, 551–568.

Yang C P; Kirschner L S; Yu L; Horwitz S B (1996): Localization of sequences that influence basal and cell type-specific activity of the murine mdr2 promoter. *Cell Growth Differ*, 7(9) p1227–37.

Yoneda K, Steinert P M (1993): Over-expression of human loricrin in transgenic mice produces a normal phenotype. *Proc Natl Acad Sci USA* 90 (22): 10754–10758.

It is claimed:

1. A transgenic mouse having integrated within its genome a MDM2 transgene operably linked to a promoter that drives expression of the transgene in skin, wherein the mouse exhibits an abnormal skin phenotype resembling ichthyosis vulgaris.

2. The transgenic mouse according to claim 1, wherein the promoter is a ubiquitous promoter.

3. The transgenic mouse according to claim 1, wherein the promoter is a heterologous promoter.

4. The transgenic mouse according to claim 1, wherein the promoter is a HCMV promoter.

5. A method of screening for a compound effective for the treatment of ichthyosis vulgaris, the method comprising (a) administering a compound to a transgenic mouse having integrated within its genome a MDM2 transgene operably linked to a promoter that drives expression of the transgene in skin, wherein the mouse exhibits an abnormal skin phenotype resembling ichthyosis vulgaris, (b) evaluating the appearance of the skin of a mouse treated according to step (a), and (c) comparing the appearance of the skin of a treated mouse to the skin of untreated control mice.

6. The method according to claim 5, wherein the skin is evaluated by visual observance.

7. The method according to claim 5, wherein the skin is evaluated by light reflectance or absorbance.

8. The method according to claim 5, wherein the skin is evaluated by histological or immunohistochemical analysis.

* * * * *

SEQUENCE LISTING

<160> NUMBER OF SEQ ID NOS: 7

<210> SEQ ID NO 1
<211> LENGTH: 23
<212> TYPE: DNA
<213> ORGANISM: Mus musculus

<400> SEQUENCE: 1
gccatgggca ataccaacat gtc                            23

<210> SEQ ID NO 2
<211> LENGTH: 23
<212> TYPE: DNA
<213> ORGANISM: Mus musculus

-continued

```
<400> SEQUENCE: 2
gactagtggt cagctagttg aag                                              23

<210> SEQ ID NO 3
<211> LENGTH: 20
<212> TYPE: DNA
<213> ORGANISM: Mus musculus

<400> SEQUENCE: 3
actcttttga aggagatcct                                                  20

<210> SEQ ID NO 4
<211> LENGTH: 20
<212> TYPE: DNA
<213> ORGANISM: Mus musculus

<400> SEQUENCE: 4
ccatcaggca catccaagcc                                                  20

<210> SEQ ID NO 5
<211> LENGTH: 20
<212> TYPE: DNA
<213> ORGANISM: Mus musculus

<400> SEQUENCE: 5
acagcgtggt ggtaccttat                                                  20

<210> SEQ ID NO 6
<211> LENGTH: 20
<212> TYPE: DNA
<213> ORGANISM: Mus musculus

<400> SEQUENCE: 6
tcctcgtgct ttacggtatc                                                  20

<210> SEQ ID NO 7
<211> LENGTH: 18
<212> TYPE: DNA
<213> ORGANISM: Mus musculus

<400> SEQUENCE: 7
tatactcaga gccggcct                                                    18
```